United States Patent [19]

Key

[11] Patent Number: 4,709,693

[45] Date of Patent: Dec. 1, 1987

[54] BELT FOR ARTHROSCOPIC TREATMENT OF AN INJURED LEG SUPPORTED BY A SURGEON

[76] Inventor: James D. Key, 10 Medical Pkwy., Dallas, Tex. 75234-7895

[21] Appl. No.: 827,501

[22] Filed: Feb. 10, 1986

[51] Int. Cl.⁴ .............................................. A61F 3/00
[52] U.S. Cl. .................................. 128/80 G; 128/94
[58] Field of Search ............... 128/94, 80 G, 133, 134, 128/87 R

[56] References Cited

U.S. PATENT DOCUMENTS

| | | | |
|---|---|---|---|
| 2,560,243 | 7/1951 | Peterson | 128/94 |
| 2,652,050 | 9/1953 | Schoeller | 128/94 |
| 3,780,729 | 12/1973 | Garnett | 128/94 |
| 4,205,666 | 6/1980 | Kapp, Jr. et al. | 128/94 |

Primary Examiner—John D. Yasko

[57] ABSTRACT

A belt holder for examination and treatment of an injured leg wherein the two hands of a surgeon are free comprising a belt worn by said surgeon, said belt having two straps to support the injured leg of a seated patient.

5 Claims, 2 Drawing Figures

BELT FOR ARTHROSCOPIC TREATMENT OF AN INJURED LEG SUPPORTED BY A SURGEON

This is a substitute for application Ser. No. 425,239 which was filed on Sept. 28, 1982 and is now abandoned.

The applicant is an Orthopedic Surgeon and second opinion physician for the Dallas Cowboy Football Team. The principal injury suffered by players during playing of a football game is a knee injury. Such an injury requires that means be provided for examination and treatment of such an injured knee. Such an injury requires support of the injured knee so that both hands of an attending surgeon are free to examine and to treat said knee injury. The applicant has developed the use of a belt, that can be fastened about the waist of a surgeon to support the injured leg of a player. Two spaced straps are provided perpendicularly to said belt which are adapted to hold the raised injured leg of a seated patient. The Garnett U.S. Pat. No. 3,780,729 in Class 128/94 was cited as prior art; however, its structure is to immobilize a shoulder by providing a chest belt with a strap for the arm of a wrist of a patient. Its structure is such as to serve a different purpose than that of applicant's strap. Since the Garnett strap is worn by the patient and its strap is adapted for shoulder immobility, it does not anticipate applicant's strap, that is worn by the doctor, so that he has his hands free to make an examination of the injury. Since the injury is painful, it is the doctor that supports the injured leg. This situation requires straps that can be readily tightened and loosened to support said leg.

Therefore, it is a principal object of this invention to provide a belt to be worn by an examining surgeon which will keep both of his hands free for examination and treatment.

It is a further object of this invention to provide cross straps for support of the leg of an injured patient.

This invention will be better understood and additional objects and advantages will become apparent from the following description of the preferred construction with reference to the accompanying drawings. Various changes may be made in the details but all such modifications within the scope of the appended claims are included in this invention.

This invention comprises a belt composed of heavy duck cloth or heavy duty plastic resin which is to be fastened about the waist of a surgeon so that ends 2 and 3 can be connected by means of Velcro patches sections 4 and 5. Straps 12 and 14 are attached at 6 and 7 so that end patches sections of Velcro 8 and 9, and 10 and 11 can be fastened about the leg of an injured patient.

Figure 1:
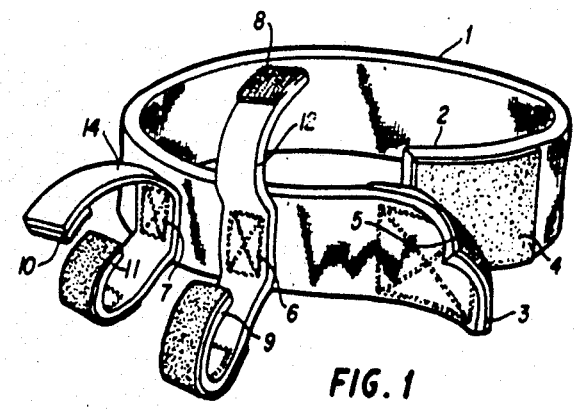
FIG. 1 is a perspective view of the belt of this invention.
Figure 2:
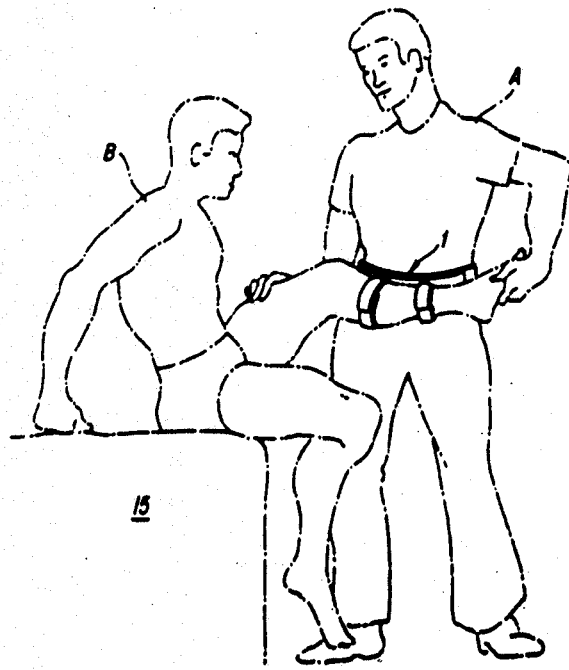
FIG. 2 is a perspective schematic view showing the belt in use.

In FIG. 2, a surgeon A fastens the belt about his waist. Then he places patient B's injured leg in the straps and fastens the Velcro pads. Now the surgeon has both hands free to perform the needed arthroscopic examination of the injured knee and can treat it without tiring the injured leg of a patient.

It is noted that the belt of this invention has been adopted by a large number of surgeons because for the first time, both hands are free for examination and treatment without tiring of said patient. This belt fills a tremendous need for which surgeons have been seeking.

Having now described my invention and in what manner the same may be used, what I claim as new and desire to protect by Letters Patent is:

1. A belt holder for the arthroscopic examination and treatment of an injured leg of a patient so as to leave both hands of a surgeon free by supporting said leg comprising a waist belt portion worn by said surgeon, and parallel perpendicularly attached straps to said belt for support of said injured leg around its calf and above its ankle.

2. The belt of claim 1 wherein the fastening of said belt and straps are Velcro pads sections.

3. The belt of claim 1 wherein the belt is composed of heavy duct cloth.

4. The belt of claim 1 wherein the belt is composed of heavy duty plastic resin.

5. A method of arthroscopically examining and treating an injured leg of a patient to leave both hands of a surgeon free for said work by use of a belt which supports the leg of said injured patient who is seated by wrapping a support belt about the waist of said surgeon and carrying said leg by means of 2 tightened straps, one around its calf and the other above its ankle which can readily be fastened with opposed Velcro patches.

* * * * *